United States Patent [19]

Weber et al.

[11] Patent Number: 5,773,658
[45] Date of Patent: Jun. 30, 1998

[54] PROCESS FOR THE PREPARATION OF N-METHYLALKYLAMINES

[75] Inventors: Jurgen Weber, Oberhausen; Detlef Kampmann, Bochum; Detlef Deymann, Essen; Claus Kniep, Oberhausen, all of Germany

[73] Assignee: Hoechst Aktiengesellschaft, Werk, Germany

[21] Appl. No.: 71,690

[22] Filed: Jun. 3, 1993

Related U.S. Application Data

[63] Continuation of Ser. No. 788,548, Nov. 6, 1991, abandoned.

[30] Foreign Application Priority Data

Nov. 7, 1990 [DE] Germany ............... 40 35 307.9

[51] Int. Cl.$^6$ ............................................. C07C 209/52

[52] U.S. Cl. .................................................. 564/473
[58] Field of Search ...................................... 564/473

[56] References Cited

FOREIGN PATENT DOCUMENTS 44-020322  9/1969  Japan ........................ 564/473

*Primary Examiner*—Brian M. Burn
*Attorney, Agent, or Firm*—Bierman, Muserlian and Lucas

[57] ABSTRACT

A process for the preparation of N-methylalkylamines of the formula $CH_3$—NH—$CH_2$—R in which R is an aliphatic radical having 1 to 3 carbon atoms, by reacting an aldehyde of the formula R—CHO with an amine of the formula R'—$NH_2$ to give a Schiff base, removing the water of reaction, and reacting the Schiff base with methylamine and hydrogen in the presence of a hydrogenation catalyst.

22 Claims, No Drawings

PROCESS FOR THE PREPARATION OF N-METHYLALKYLAMINES

This application is a continuation of U.S. patent application Ser. No. 788,548 filed Nov. 6, 1991, now abandoned.

This application claims the Priority of German Application P 40 35 307.9, filed Nov. 7, 1990.

The present Invention relates to a process for the preparation of N-methylalkylamines of the formula $CH_3$—NH—$CH_2$—R in which R is an aliphatic radical. Their properties make amines of this type important for a number of technical applications. They are useful as intermediates in the preparation of crop-protection agents, pharmaceuticals, additives, antioxidants, anti-corrosion agents, and catalysts for the preparation of plastics, e.g. epoxy resins and polyurethanes.

BACKGROUND OF THE INVENTION

The preparation of N-methylalkylamines from methylamine and an aldehyde of the formula R—CHO, or from an amine of the formula R—$CH_2$—$NH_2$ and formaldehyde, followed by subsequent hydrogenation of the resultant reaction products is not as successful as desired. In both process variants, numerous by-products form at the hydrogenation step as a consequence of transalkylation reactions.

Thus, the process for the preparation of N-methyl-n-propylamine which is described by Arthur C. Cope, et al. in J. Am. Chem. Soc. 79, 4720–4729 (1957), using a platinum catalyst in the hydrogenation of the reaction product of aldehyde and a primary amine gives a yield of valuable products of only 25% (cf. page 4727, Table IV, 1st line).

The preparation of N-methyl-n-butylamine carried out by Henry R. Henze and David D. Humphreys in J. Am. Chem. Soc. 64, 2878–2880 (1942) by reacting methylamine with n-butanal and subsequently hydrogenating the resultant azomethine (Schiff base) in the presence of Raney nickel as catalyst gives only 26% of N-methyl-n-butylamine in addition to significant amounts of N-methyl-di-n-butyl-amine (cf. Table I on page 2879, 1st line).

If the preparation of N-methyl-n-butylamine is modified by carrying out the hydrogenation of the reaction product of methylamine and n-butanal by means of $LiAlH_4$, as indicated by Armiger H. Sommers and Sharon E. Aaland in J. Org. Chem. 21, 484–485 (1956), a yield of 55% is obtained (cf. page 484, right-hand column, Table I, 1st line).

There is thus a demand for a process which, on the one hand, uses readily accessible starting materials and, on the other hand, can be carried out on an industrial scale at acceptable cost. Furthermore, the process results in a reduction in the amount of undesired by-products and simultaneously in an increase in the yield of valuable product.

SUMMARY OF THE INVENTION

This object is achieved by a process for the preparation of amines of the formula $CH_3$—NH—$CH_2$—R, in which R is an aliphatic radical having 1 to 3 carbon atoms, which comprises reacting an aldehyde of the formula R—CHO with an amine of the formula R'—$NH_2$, in which R' is a straight-chain or branched aliphatic radical having 6 to 12 carbon atoms, to give a Schiff base, removing the water of reaction, and reacting the Schiff base with methylamine and hydrogen in the presence of a hydrogenation catalyst.

DETAILED DESCRIPTION OF THE INVENTION

The reaction of an aldehyde of the formula R—CHO with an amine of the formula R'—$NH_2$ gives the corresponding Schiff base (azomethine) with formation of water. The reaction proceeds even at relatively low temperatures, but temperatures of from 20° to 80° C., in particular from 30° to 70° C., preferably from 40° to 60° C., are used in order to limit the reaction time. There is usually no need to use an additional solvent in the preparation of the azomethine. The reaction mixture formed as a consequence of the reaction between the aldehyde and the amine is produced in heterogeneous form. The upper, organic phase contains the Schiff base, while the water of reaction deposits virtually quantitatively in the lower phase.

Addition of a limited amount of a solvent is only to be recommended if the removal of the water of reaction does not take place to the desired extent. Examples of suitable solvents are toluene, xylene and cyclohexane.

The aldehydes used are advantageously acetaldehyde, propionaldehyde, isobutyraldehyde, and n-butyraldehyde, in particular acetaldehyde, propionaldehyde, and butyraldehyde, most preferably propionaldehyde.

Suitable amines of the formula R'—$NH_2$ are straight-chain or branched aliphatic amines in which R' is a radical having 6 to 12, in particular 7 to 12, preferably 8 to 10, carbon atoms. Suitable amines include n-hexylamine, n-heptylamine, n-octylamine, 2-ethylhexylamine, n-nonylamine, n-decylamine, n-undecylamine, n-dodecylamine, i-hexylamine, i-heptylamine, i-octylamine, i-nonylamine, i-decylamine, i-undecylamine, i-dodecylamine, and mixtures thereof. The amines can be prepared industrially by hydroformylation of an appropriate olefin and subsequent reaction of the aldehyde formed with ammonia and hydrogen.

The formation of the Schiff base requires, in accordance with the stoichiometry of the reaction, one mole of amine per mole of aldehyde. However, it is advantageous to use the amine in excess relative to the aldehyde. From 1.02 to 2.0 mole, in particular 1.05 to 1.8 mole, most preferably 1.1 to 1.5 mole, of the amine of the formula R'—$NH_2$ is employed per mole of the aldehyde of the formula R—CHO.

The reaction of the aldehyde with the amine can be carried out continuously or batchwise. The water of reaction can be removed at temperatures of from 10° to 80° C., in particular from 15° to 50° C., preferably from 20° to 35° C., either during the reaction or after completion of the formation of the azomethine.

The azomethine formed is subsequently reacted with methylamine and hydrogen in the presence of a hydrogenation catalyst. The reaction proceeds particularly well if methylamine is used in a sufficient stoichiometric excess relative to the Schiff base. It is advisable to employ from 4 to 40 mole, in particular from 5 to 30 mole, preferably from 10 to 20 mole, of methylamine per mole of Schiff base.

In order to prepare the corresponding N-methylalkylamine from the Schiff base, one mole of hydrogen is required per mole of azomethine in accordance with the stoichiometry of the reaction. However, the hydrogen is usually employed in a sufficient excess. Since the elevated pressure necessary for the reaction is produced by addition of hydrogen, a sufficient amount of hydrogen is introduced into the reaction in this way.

The Schiff base, methylamine and hydrogen are reacted at from 80° to 200° C., in particular from 90° to 180° C., preferably from 100° to 160° C., and at from 5 to 25 MPa, in particular from 8 to 20 MPa, preferably from 10 to 15 MPa.

A further advantage of the process according to the invention is that it is not limited to the use of specific catalysts, but instead allows the use of a large number of conventional hydrogenation catalysts. The catalyst can be used in pelletized form or as a suspension. The catalysts may be supported or unsupported. They contain Ni, Co, Cu, Mn, Fe, Rh, Pt, and/or Pd; in particular Ni, Co, Cu and/or Pd; preferably Ni, Co and/or Pd. In addition, if desired, customary additives and promoters, for example alkaline earth metal oxides, $SiO_2$, $Al_2O_3$, $MnO_2$ and/or $Cr_2O_3$, may be included.

It is advantageous to use supported catalysts. Suitable supports are $Al_2O_3$, $SiO_2$, silica gel, siliceous earth, activated charcoal, and/or pumice stone, in particular $SiO_2$ silica gel, siliceous earth, and/or activated charcoal. The supported catalysts usually contain from 10 to 75% by weight, in particular from 20 to 70% by weight, preferably from 40 to 65% by weight of Ni, Co, Cu, Mn, and/or Fe, based on the total catalyst composition. Particularly proven catalysts are those containing from 20 to 70% by weight, in particular from 40 to 65% by weight, of Ni and/or Co, based on the total catalyst composition.

The noble metal catalysts which are suitable for the reaction are usually supported and have a metal content of from 0.1 to 20% by weight, in particular from 0.2 to 15% by weight, preferably from 0.5 to 10% by weight, based on the total catalyst composition. Suitable noble metals are Rh, Pt, and/or Pd, in particular Pt and/or Pd, most preferably Pd. Recommended supports are shaped materials based on $Al_2O_3$, $_{SiO2}$, activated charcoal, silica gel, kieselguhr, and/or pumice stone; in particular $Al_2O_3$, $_{SiO2}$, silica gel, kieselguhr, and/or activated charcoal; preferably silica gel, kieselguhr, and/or activated charcoal.

The Schiff base, the methylamine and the hydrogen are mixed intimately and reacted in the presence of the hydrogenation catalyst. The reaction can be carried out batchwise or continuously. A particularly simple batchwise procedure is to carry out the reaction using a suspended hydrogenation catalyst. The Schiff base, the methylamine, and the catalyst are introduced into a pressure-tight vessel. Hydrogen is injected, and the mixture is warmed with stirring. As soon as the absorption of hydrogen is complete, the reaction is terminated. The catalyst is subsequently removed, for example by filtration and/or centrifugation. The reaction mixture which remains can then be worked up by distillation.

The continuous reaction of the Schiff base with methylamine and hydrogen is particularly simple to carry out using pressure-tight tubular reactors which contain the hydrogenation catalyst in pelletized form arranged as a fixed bed. The starting materials are fed either to the top or bottom of the reactor; depending on the type of addition, one refers to a trickle or pool procedure. If the trickle procedure is used, the reaction product leaves the reactor at the bottom and, if the pool procedure is used, the reaction mixture exits at the head of the reactor. If desired, some of the reaction mixture can also be recycled into the reactor. The process is particularly suitable for the preparation of methyl-n-propylamine. A particularly suitable amine is 2-ethylhexylamine.

The examples below illustrate the invention without limiting it.

EXPERIMENTAL PART

Example 1: Preparation of N-methyl-n-propylamine.

1,350 g (10.5 mole) of 2-ethylhexylamine are introduced into a three-neck flask (volume 4 liters) equipped with a stirrer, thermometer, dropping funnel, and a reflux condenser. 551 g (9.5 mole) of propanal are added dropwise with stirring over the course of 2 hours at a rate such that a temperature of 45° to 50° C. is maintained. When the addition of propanal is complete, the mixture is stirred for a further 2 hours, the temperature slowly dropping back to room temperature. The stirring is terminated. Two phases form, which can be easily separated.

There are 157 g of the lower, water-containing phase, corresponding to 92% of the theoretical amount of water of reaction. The upper, organic phase, which contains the azomethine (Schiff base) formed from propanal and 2-ethylhexylamine, is transferred to an autoclave and reacted with methylamine in the presence of 5% by weight of a nickel catalyst which contains about 50 to 53% by weight of Ni and about 25 to 30% by weight of kieselguhr as a support. 10 mole of methylamine are employed per mole of azomethine.

The reaction is carried out at 140° C. and 10 MPa over a period of 3 hours. Gas-chromatographic analysis of the reaction mixture produced indicates the following composition, without taking into account methylamine employed in excess and the liberated 2-ethylhexylamine:

TABLE 1

Composition of the reaction mixture
(gas-chromatographic analysis without $CH_3NH_2$ and 2-ethylhexylamine)

| Preliminary fraction | 5.4% by weight |
| N-Methyl-n-propylamine | 73.6% by weight |
| Intermediate fraction | 8.7% by weight |
| N-Propyl-2-ethylhexylamine | 12.3% by weight |

Distillation (atmospheric pressure, column having 24 theoretical plates) gives N-methyl-n-propylamine in a purity of >99%. The recovered 2-ethylhexylamine can be recycled into the synthesis (azomethine formation).

Comparative Experiment 1: Preparation of N-methyl-n-propylamine. 815 g of a 40% strength aqueous methylamine solution three-neck flask (volume 4 liters) equipped with stirrer, thermo dropping funnel, and reflux condenser. 551 g (9.5 mole) of propanal are added dropwise over the course of 2 hours, as indicated in Example 1, the mixture is stirred for 2 hours after completion of the addition of propanal, the aqueous phase is separated from the organic phase. Thereafter, the upper phase is separated from the organic phase, and the upper phase containing the azomethine (Schiff base) formed from the propanal and methylamine is transferred into an autoclave. The reaction is carried out at 140° C. and 10 MPa over a period of 3 hours in the presence of .5% by weight of the catalyst used in Example 1. Gas-chromatographic analysis of the reaction mixture produced indicates the following composition, without taking into account methylamine:

TABLE 2

Composition of the reaction mixture
(gas-chromatographic analysis without $CH_3NH_2$)

| Preliminary fraction | 0.2% by weight |
| N-Methyl-n-propylamine | 11.2% by weight |
| N,N-Dimethyl-n-propylamine | 1.8% by weight |
| Di-n-Propylamine | 0.6% by weight |

TABLE 2-continued

| Composition of the reaction mixture (gas-chromatographic analysis without $CH_3NH_2$) | |
| --- | --- |
| N-Methyl-di-n-propylamine | 5.1% by weight |
| Higher-boiling components | 80.0% by weight |

Distillation (atmospheric pressure, column having 24 theoretical plates) gives N-methyl-n-propylamine in a purity of only 84%, since removal of the N,N-dimethyl-n-propylamine obtained due to transalkylation is not possible due to its virtually identical boiling point.

Example 2: Preparation of N-methylethylamine.

The procedure of Example 1 was followed except that 418 g (9.5 mole) of acetaldehyde were used in place of propanol as the starting material. Gas-chromatographic analysis of the reaction mixture produced indicates the following composition, without taking into account methylamine employed in excess and the liberated 2-ethylhexylamine:

TABLE 3

| Composition of the reaction mixture (gas-chromatographic analysis without $CH_3NH_2$ and 2-ethylhexylamine) | |
| --- | --- |
| Preliminary fraction | 1.5% by weight |
| N-Methylethylamine | 80.8% by weight |
| N-Methyl-n-butylamine | 0.8% by weight |
| 2,4,6-Trimethyl-1,3-5-trioxane | 4.6% by weight |
| N-2-Ethylhexylethylamine | 12.3% by weight |

Comparative Experiment 2: Preparation of N-methylethylamine.

The procedure is as indicated in Comparative Experiment 1, but 418 g (9.5 mole) of acetaldehyde are employed instead of propanal. Gas-chromatographic analysis of the reaction mixture produced indicates the following composition, without taking into account methylamine:

TABLE 4

| Composition of the reaction mixture (gas-chromatographic analysis without $CH_3NH_2$) | |
| --- | --- |
| Preliminary fraction | 1.5% by weight |
| N-Methylethylamine | 34.5% by weight |
| N,N-Diethylmethylamine | 0.9% by weight |
| N-Methyl-n-butylamine | 13.8% by weight |
| 2,4,6-Trimethyl-1,3,5-trioxane | 4.3% by weight |
| N-Ethyl-N-methyl-n-butylamine | 7.2% by weight |
| Higher-boiling components | 37.8% by weight |

Example 3: Preparation of N-methyl-n-butylamine.

The procedure of Example 1 was followed except that 685 g (9.5 mole) of n-butanal were used in place of propanol as the starting material. Gas-chromatographic analysis of the reaction mixture produced indicates the following composition, without taking into account methylamine employed in excess and the liberated 2-ethylhexylamine:

TABLE 5

| Composition of the reaction mixture (gas-chromatographic analysis without $CH_3NH_2$ and 2-ethylhexylamine) | |
| --- | --- |
| Preliminary fraction | 0.6% by weight |
| Components | 7.3% by weight |

TABLE 5-continued

| Composition of the reaction mixture (gas-chromatographic analysis without $CH_3NH_2$ and 2-ethylhexylamine) | |
| --- | --- |
| Intermediate fraction | 0.3% by weight |
| N-Methyl-n-butylamine | 82.3% by weight |
| Higher-boiling components | 9.5% by weight |

Comparative Experiment 3: Preparation of N-methyl-n-butylamine.

The procedure is as set forth in Comparative Experiment 1, except that 685 g (9.5 mole) of n-butanal is employed instead of propanal. Gas-chromatographic analysis of the reaction mixture produced indicates the following composition, without taking into account methylamine:

TABLE 6

| Composition of the reaction mixture (gas-chromatographic and analysis without $CH_3NH_2$) | |
| --- | --- |
| Preliminary fraction | 2.0% by weight |
| N-Methyl-n-butylamine | 71.5% by weight |
| N,N-Dimethyl-n-butylamine | 1.0% by weight |
| N,N-Di-n-butylmethylamine | 9.3% by weight |
| N-Methyl-2-ethylhexylamine | 6.0% by weight |
| N,N-Di-n-butyl-2-ethylhexylamine | 6.2% by weight |
| Higher-boiling components | 4.0% by weight |

What is claimed is:

1. A process for the preparation of an amine of the formula $CH_3$—NH—$CH_2$—R, wherein R is an aliphatic radical having 1 to 3 carbon atoms, comprising a first reaction of an aldehyde of the formula R—CHO with an amine of the formula R'—$NH_2$, wherein R' is a straight or branched chain aliphatic radical having 6 to 12 carbon atoms, to produce a Schiff base and water of reaction, removal of said water, and a second reaction of said base with methylamine and hydrogen in the presence of a hydrogenation catalyst.

2. The process of claim 1 wherein said first reaction is carried out at a first reaction temperature of 20° to 80° C.

3. The process of claim 2 wherein said first reaction temperature is 40° to 60° C.

4. The process of claim 1 wherein a molar ratio of said amine to said aldehyde is 1.02 to 2.0.

5. The process of claim 4 wherein said molar ratio is 1.1 to 1.5.

6. The process of claim 1 wherein there are 4 to 40 moles of methylamine per mole of said base.

7. The process of claim 6 wherein there are 5 to 30 moles of methylamine per mole of said base.

8. The process of claim 7 wherein there are 10 to 20 moles of methylamine per mole of said base.

9. The process of claim 1 wherein said removal takes place at a removal temperature of 10° to 80° C.

10. The process of claim 9 wherein said removal temperature is 20° to 35° C.

11. The process of claim 1 wherein said second reaction is carried out at a second reaction temperature of 80° to 200° C.

12. The process of claim 11 wherein said second reaction temperature is 100° to 160° C.

13. The process of claim 1 wherein said second reaction is carried out under a second reaction pressure of 5 to 25 MPa.

14. The process of claim 13 wherein said second reaction pressure is 10 to 15 MPa.

15. The process of claim 1 wherein said aldehyde is propionaldehyde.

16. The process of claim 1 wherein said R' has 8 to 10 carbon atoms.

17. The process of claim 1 wherein said amine is selected from the group consisting of n-hexylamine, n-heptylamine, n-octylamine, 2-ethylhexylamine, n-nonylamine, n-decylamine, n-undecylamine, n-dodecylamine, i-hexylamine, i-heptylamine, i-octylamine, i-nonylamine, i-decylamine, i-undecylamine, i-dodecylamine, and mixtures thereof.

18. The process of claim 17 wherein said amine is 2-ethylhexylamine.

19. The process of claim 1 wherein said hydrogenation catalyst contains a metal selected from the group consisting of Ni, Co, Cu, Mn, Fe, Rh, Pt, Pd, and combinations thereof.

20. The process of claim 19 wherein said metal is selected from the group consisting of Ni, Co, Pd, and combinations thereof.

21. The process of claim 20 wherein said catalyst contains a catalyst amount of 20 to 70% by weight of nickel based on said hydrogenation catalyst.

22. The process of claim 21 wherein said catalyst amount is 40 to 65% by weight.

* * * * *